United States Patent [19]

Feldner et al.

[11] Patent Number: 4,552,973

[45] Date of Patent: Nov. 12, 1985

[54] PROCESS FOR THE PREPARATION OF DIMETHYLDICHLOROSILANE

[75] Inventors: Kurt Feldner; Wolfgang Grape, both of Cologne, Fed. Rep. of Germany

[73] Assignee: Bayer Aktiengesellschaft, Leverkusen, Fed. Rep. of Germany

[21] Appl. No.: 713,501

[22] Filed: Mar. 19, 1985

[30] Foreign Application Priority Data

Mar. 23, 1984 [DE] Fed. Rep. of Germany ....... 3410644

[51] Int. Cl.$^4$ .............................................. C07F 7/12
[52] U.S. Cl. .................................................. 556/469
[58] Field of Search ........................................ 556/469

[56] References Cited

U.S. PATENT DOCUMENTS

| | | |
|---|---|---|
| 2,647,136 | 7/1953 | Sauer .................................... 556/469 |
| 2,647,912 | 8/1953 | Barry et al. ......................... 556/469 |
| 2,717,257 | 9/1955 | Bluestein ............................ 556/469 |
| 3,384,652 | 5/1968 | Hamilton ........................... 556/469 |
| 4,477,631 | 5/1984 | Faure et al. ........................ 556/469 |

Primary Examiner—Paul F. Shaver
Attorney, Agent, or Firm—Sprung, Horn, Kramer & Woods

[57] ABSTRACT

A process for the preparation of dimethyldichlorosilane from the low-boiling and high-boiling by-products of the direct synthesis of methylchlorosilane, comprising reacting methyltrichlorosilane simultaneously with the low-boiling components having a high content of methyl groups and with the high-boiling non-cleavable components, in the presence of a catalyst, at a temperature between about 250° C. and 400° C. and under a pressure of up to 100 bar.

4 Claims, No Drawings

PROCESS FOR THE PREPARATION OF DIMETHYLDICHLOROSILANE

The present invention relates to a process for the preparation of dimethyldichlorosilane from unavoidable products of the direct synthesis of methylchlorosilanes, in which low-boiling components having a high methyl content as well as non-cleavable high-boiling residues together with methyltrichlorosilane are converted to, in particular, dimethyldichlorosilane, which is a valuable compound.

In the preparation of dimethyldichlorosilane by direct synthesis (Müller-Rochow method), a substantial amount of unavoidable products are formed in addition to the desired product. The direct method is described in the patent literature, for example in U.S. Patent Specifications Nos. 2,380,995 and 2,488,487.

The most important by-product formed, in terms of amount, is methyltrichlorosilane, which is formed in amounts which cannot be utilized economically for the preparation of silicones. The bulk of the methyltrichlorosilane is currently used for the preparation of pyrogenic silica; however, this process constitutes an unsatisfactory provisional solution, since valuable methyl groups introduced into the system undergo combustion to form $CO_2$ and water.

In addition to methyltrichlorosilane, other by-products are formed in the direct synthesis of dimethyldichlorosilane:

(a) Unavoidable low-boiling products having a boiling point below 40° C., such as, for example, tetramethylsilane (TMS), dimethylmonochlorosilane and 2-methylbut-2-ene.

(b) Compounds which have a higher boiling point than the monosilanes, that is to say a boiling point from above 70° C. to about 180° C.; these compounds are referred to below either as "residue" or as "high-boiling fraction". This residue is a complex mixture of compounds which contain SiSi, SiOSi and SiCH$_2$Si bonds in the molecules. Typical residues are described in U.S. Patent Specifications Nos. 2,599,435 and 2,681,355.

A large number of methods have been suggested for working up these unavoidable products (see, for example, German Offenlegungsschrift (German Published Specification) No. 2,950,402; R. Calas et al., Journal of Organometallic Chemistry, 225, 117 (1982)).

In certain circumstances, the compounds trimethylmonochlorosilane and methyldichlorsilane, which are normally included among the useful products in the direct method, are also formed in amounts which cannot be utilized economically.

According to U.S. Patent Specification No. 2,786,861, alkylchlorosilanes were converted in the presence of a catalyst, such as aluminum chloride, and it was found that this conversion could be carried out in an advantageous manner at relatively low temperatures if a compound which promotes this conversion, that is to say a hydrogenosilane, was used. A serious disadvantage of this method is that extremely large amounts of aluminum chloride are required as the catalyst, at least 10%, relative to the silane mixture to be converted.

The transfer of methyl groups from tetramethylsilane to hexachlorodisilane or 1,1,2,2-tetrachloro-1,2-dimethyldisilane or mixtures of disilanes having a high chlorine content is described in, for example, German Offenlegungsschrift (German Published Specification) No. 3,208,829. The catalyst used in this case is an organoaluminum chloride which, however, is converted to the known catalyst AlCl$_3$ by hydrogen chloride gas fed simultaneously into the reaction mixture.

German Offenlegungsschrift (German Published Specification) No. 3,314,734 describes the reaction of disilanes which have a high methyl content and do not undergo cleavage reactions, with methyltrichlorosilane, with the aim of producing dimethyldichlorosilane and disilanes which have a high chlorine content and undergo cleavage reactions. Since a declared aim of this process is to convert disilanes which cannot undergo cleavage reactions to cleavable disilanes, the reaction is restricted to temperatures up to about 175° C. and pressures up to 3 atmospheres, in order to avoid side reactions. Possible side reactions are in principle familiar to one skilled in the art. Free-radical reactions of polysilanes are described in, for example, German Auslegeschrift (German Published Specification) No. 2,618,246, and the possible participation of Lewis acids, such as, for example, aluminum chloride, in such free-radical reactions is described in, for example, German Offenlegungsschrift (German Published Specification) No. 3,136,786. Under the reaction conditions which are described in DOS (German Published Specification) No. 3,314,734 as being advantageous, the stated side reactions do not take place. However, the consequence of choosing the reaction conditions 175° C./3 atmospheres is that substantial amounts of aluminum chloride are required as catalyst. In some of the examples published, the amount of catalyst is about 20%, relative to the silane mixture employed, without taking into account the hydrogeniosilane added as a promoter.

The catalyst can be worked up only with considerable effort, and this procedure is therefore uneconomical. Furthermore, a continuous procedure with homogeneous catalysis is scarcely possible for such a large amount of catalyst, owing to the low solubility of the aluminum chloride in the reaction mixture. Hence, the process described in DOS (German Published Specification) No; 3,314,734 is hardly suitable as a method of preparing dimethyldichlorosilane in a continuously working reactor.

It was therefore the object of the present invention to provide a method for reducing the amounts of waste products in the direct synthesis of methylchlorosilane, these waste products hitherto essentially being destroyed.

It was furthermore the object of the present invention to find a process for the preparation of dimethyldichlorosilane from unavoidable products of the direct synthesis of methylchlorosilane.

It was furthermore the object of the present invention reasonably to utilize the methyl groups which are present in bonded form in the low-boiling residues, such as tetramethylsilane (TMS) and dimethylchlorosilane, and in the high-boiling non-cleavable residue, and have hitherto been destroyed.

A further object of the present invention is to convert the compound methyldichlorosilane, if required, to valuable compounds.

Finally, it is intended that the process for the preparation of dimethyldichlorosilane from unavoidable products of the direct synthesis of methylchlorosilane be designed in such a way that it can be carried out by a continuous procedure.

The present invention therefore relates to a process for the preparation of dimethyldichlorosilane from the unavoidable low-boiling and high-boiling products of the direct synthesis of methylchlorosilane, characterized in that methyltrichlorosilane, together with the low-boiling fractions having a high content of methyl groups and the high-boiling non-cleavable fractions, is converted at temperatures between 250° C. and 400° C. and under pressures up to 100 bar, in the presence of a catalyst.

By means of the process according to the invention, "waste products", as obtained in the Rochow synthesis, are converted in high yield to the valuable compound dimethyldichlorosilane by reaction with one another in the presence of a catalyst.

Any fraction obtained from the Rochow-Muller process having a boiling point of less than 40° C. and having a high methyl content can be employed in the process according to the invention. As a rule, these fractions contain tetramethylsilane, dimethylmonochlorosilane, 2-methylbut-1-ene and 2-methylbut-2-ene as principal components. Methylchloride, ethyl chloride, 2-methylbutane, SiHCl$_3$, SiCl$_4$ and other compounds also occur as by-products. The composition can vary to a great extent, and is dependent on the procedure of the direct synthesis of methylchlorosilanes. The two compounds TMS and dimethylmonochlorosilane are to be regarded as having a high methyl content, and are capable of transferring methyl groups to methyltrichlorosilane, if required also to SiCl$_4$. When the conditions according to the invention are maintained, TMS donates two methyl groups and is consequently converted to the valuable compound dimethyldichlorosilane, via, for example, the following equation:

$$(CH_3)_4Si + 2CH_3SiCl_3 \rightarrow 3(CH_3)_2SiCl_2$$

Dimethylmonochlorosilane can also transfer methyl groups to methyltrichlorosilane.

U.S. Patent Specification No. 2,786,861 and DOS (German Published Specification) No. 3,314,734 have stated that, in processes which comprise a CH$_3$—Cl exchange in silanes, the addition of a hydrogenosilane in addition to the actual catalyst is necessary for the reaction. In the process according to the invention, a special addition is not required since hydrogenosilanes are already present in sufficient amounts in the low-boiling fraction used, which has a high methyl content. An example of such a hydrogenosilane compound which promotes the reaction is dimethylmonochlorosilane, which is present in the low-boiling fraction. However, the compound SiHCl$_3$, which was mentioned above as a component of the low-boiling fraction, also has an action in the desired direction. According to the present invention, the compound methyldichlorsilane can also be added to the reaction mixture, in addition to the low-boiling fraction having a high methyl content. Methyldichlorosilane is likewise to be regarded as a compound which promotes the desired reaction.

The hydrocarbon compounds which are also present in the low-boiling fraction do not interfere in the reaction according to the invention, and can be used for another purpose (for example combustion) after the crude product obtained by the process according to the invention has been worked up.

The non-cleavable disilane fraction having a high methyl content is obtained after the high-boiling residue which is obtained in the direct synthesis of methylchlorosilanes has been separated into monosilanes and a non-cleavable fraction by known cleavage reactions.

In the direct method, methyl chloride is reacted with silicon or an alloy or mixture of silicon and a metal at elevated temperature, in order to produce dimethyldichlorosilane. After the monomeric methylsilanes and methylchlorosilanes which have boiling points up to about 70° C. have been removed from the reaction product, a residue, a high-boiling fraction, remains. It has been found that valuable fractions have remained in this residue, and various methods have been used in order to utilise the silane present in this residue.

U.S. Patent Specifications Nos. 2,709,176 and 2,842,580 describe processes for the cleavage of the polysilanes present in the residue. While the polysilanes having a high halogen content can be readily cleaved, the polysilanes having a high alkyl content can be cleaved only under certain conditions. Thus, for example, hexamethyldisilane, chloropentamethyldisilane and 1,2-dichlorotetramethyldisilane are disilanes of the stated type which have a high alkyl content.

In contrast, 1,2,2-trichlorotrimethyldisilane, 1,1,2,2-tetrachlorodimethyldisilane and 1,1-dichlorotetramethyldisilane are disilanes which can be cleaved more readily than the stated disilanes having a high alkyl content, using the customary methods. All of the above-mentioned disilanes can be found in the residue obtained in the direct method for the preparation of alkylhalogenosilanes.

By carrying out one of the customary cleavage reactions described in the abovementioned U.S. Patent Specifications, 1,2,2-trimethyltrichlorodisilane, 1,1,2,2-tetrachlorodimethyldisilane and 1,1-dichlorotetramethyldisilane are converted to monomeric silanes and hence removed from the high-boiling residue. The disilanes having a high alkyl content, such as hexamethyldisilane, chloropentamethyldisilane or 1,2-dichlorotetramethylsilane remain as a non-cleavable fraction, together with other compounds such as methylethyldichlorosilane, methylpropyldichlorosilane, disiloxanes, trisilanes and silalkylenes, such, for example, (CH$_3$)$_2$ClSiCH$_2$SiCH$_3$Cl$_2$ The methyl groups present in this high-boiling non-cleavable fraction having a high methyl content are employed in the process according to the invention to convert methyltrichlorosilane to dimethyldichlorosilane.

If the non-cleavable fraction contains, for example, hexamethyldisilane, this reacts with methyltrichlorosilane under the conditions according to the invention, to form 1,1,2,2-tetrachlorodimethyldisilane and dimethyldichlorosilane.

Typical reactions with the residues described above, which can be carried out according to the invention, can be represented by, for example, the following equations.

 (I)

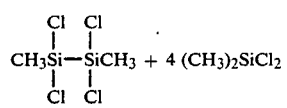

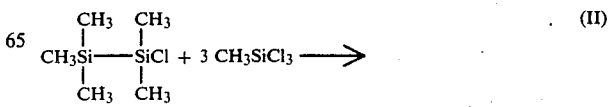 (II)

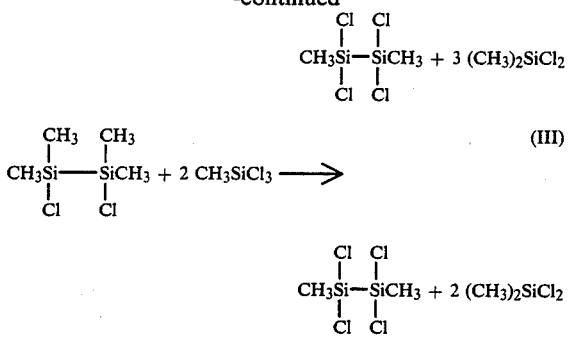

$$\text{(III)}$$

Residues of trichlorotrimethyldisilane and tetrachlorodimethyldisilane which may still be present in the non-cleavable fraction when cleavage has been carried out incompletely do not interfere with the reaction according to the invention. If, on the other hand, the process is carried out under conditions according to the invention, it is even possible for trichlorotrimethyldisilane to transfer a methyl group to methyltrichlorosilane, and consequently to be converted to tetrachlorodimethyldisilane.

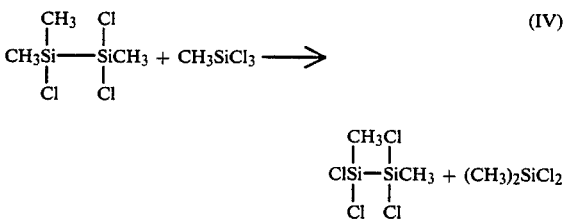

$$\text{(IV)}$$

In carrying out the process under the conditions according to the invention, the end product obtained comprises the disilane having a high chlorine content in addition to the desired dimethyldichlorosilane. This disilane having a high chlorine content can be contaminated with the catalyst, aluminum chloride, and with other high-boiling compounds formed because of freeradical side reactions, and is in general not isolated any further but can be eliminated in a relatively simple manner in conjunction with the stated impurities.

The amounts of the individual unavoidable products of the direct synthesis of methylchlorosilanes which are employed are not critical. In general, the amounts of the low-boiling fraction having a high methyl content and of the non-cleavable residue having a high methyl content will be adapted to the circumstances of production. Since both the amount of the low-boiling fraction and the amount of the non-cleavable residue are dependent on the procedure in the direct synthesis of methylchlorosilanes, the particular amounts of the two fractions which are employed can vary within a certain range. Each fraction can also be used alone. In general, all available, unavoidably produced fractions which have not been used hitherto will be brought to reaction with methyltrichlorosilane.

The amount of methyltrichlorosilane employed may depend on the amounts and on the particular compositions of the unavoidable product fractions employed.

Using the equations described above, one skilled in the art will be able to calculate the particular amount of methyl groups which is available in the unavoidable product fractions for reaction with methyltrichlorosilane, and can then employ the stoichiometric amount of methyl trichlorosilane, which can be converted to dimethyldichlorosilane by the particular amount of methyl groups present.

However, it is generally preferable to employ a molar excess of the methyltrichlorosilane. In the most preferable embodiment, the amount of methyltrichlorosilane is about 1.5 to about 4 moles per mole of methyl groups available.

If required, methyltrichlorosilane can also be replaced completely or at least partially by $SiCl_4$.

Any suitable catalyst which promotes the exchange of the alkyl groups of a silane molecule with halogen atoms of another silane molecule can be used in the process according to the invention. The preferred catalysts for the process according to the invention are aluminum trichloride or compounds of aluminum trichloride which can be decomposed to aluminum trichloride under the reaction conditions. However, it is also possible to employ any equivalent catalyst which promotes the exchange of the alkyl groups with the halogen atoms in the silanes, disilanes and polysilanes.

Examples of other catalysts which in the conversion of the disilanes which have a high alkyl content, which are present in the residues obtained in the preparation of alkylhalogenosilanes and which are reacted with the alkyltrihalogenosilanes are sodium aluminum tetrachloride, copper(I) chloride, boric acid and boron trifluoride.

In general, however, aluminum trichloride is the preferred and most economical catalyst, which is more effective than the other catalysts for the preparation of dimethyldichlorosilane by the process according to the invention.

The amount of catalyst which is employed in the process according to the invention is not particularly critical. However, the catalyst is preferbly used in a concentration of about 0.5 to about 7% by weight, preferably about 1–4%, relative to the weight of the total silane mixture employed. Since, in a particularly preferred embodiment, the catalyst is dissolved in the silane mixture to give a homogeneous solution and is pumped together with the silane mixture homogeneously into a continuously operated reactor, and should leave the reactor together with the silane mixture when the reaction is complete, it is particularly preferble to employ the catalyst in amounts which can be dissolved in the silane mixture. In this particularly preferred embodiment, therefore, the amount of catalyst will not exceed about 4%.

In another embodiment of the process according to the invention, for the preparation of dimethyldichlorosilane from unavoidable products of the direct synthesis of methylchlorosilane, it is also possible, under certain circumstances, to add methyldichlorosilane to the reaction mixture. Methyldichlorosilane serves on the one hand as a reaction-promoting cocatalyst in the process according to the invention, but on the other hand can be converted to the useful product dimethyldichlorosilane under the conditions according to the invention, since an internal exchange of $CH_3$ with H approximately according to the equation $$2CH_3SiHCl_2 \rightarrow (CH_3)_2SiCl_2 + SiH_2Cl_2$$

can take place (see R. Calas et al., Journal of Organometallic Chemistry 206, 279 (1981)).

Another important by-product of the direct synthesis is trimethylmonochlorosilane, which is important in silicone chemistry as a reagent which forms terminal groups and hence controls the degree of polymerization. If necessary, this product, too, can be converted according to the invention.

The temperature at which the process according to the invention is carried out can vary, but the reaction is usually carried out at a temperature above 250° C. The reaction is preferably carried out at temperatures between 300° C. and 400° C.

The process according to the invention is carried out under elevated pressure. The reaction is therefore carried out in pressure vessels such as, for example, autoclaves or a similar apparatus. In the preferred embodiment, the process according to the invention is carried out under pressures of up to 100 bar, and the range between 30 and 60 bar is particularly preferred.

The duration of the reaction is not particularly critical and can be determined without difficulties by one skilled in the art.

In the preferred embodiment, the low-boiling components having a high methyl content and the non-cleavable disilanes are brought into contact with the methyltrichlorosilane in the presence of the catalyst for about 0.2 h to about 8 h in order to obtain the desired useful product. The reaction time naturally depends to some extent on the temperature employed and on the pressure. In the particularly preferred embodiment, the duration of the reaction is between 0.3 and 3 h.

The process according to the invention can be carried out batchwise, semicontinuously or continuously. In the preferred form, the process is carried out continuously. In the most preferable form, the catalyst is dissolved in the reaction mixture, and is pumped homogeneously, together with the reaction mixture, continuously into an autoclave heated to 250° to 400° C. The pressure depends on the reaction temperature, and is about 30 to 100 bar, preferably 30 to 60 bar. The reaction time is controlled by the pumping rate, so that the sojourn time of the reaction mixture in the reactor is between 0.3 and 3 h. The term "reactor" also includes a cascade consisting of a plurality of autoclaves. When the reaction is complete, the product mixture is brought to atmospheric pressure, and is worked up in a manner which is known per se, in order to isolate the dimethyldichlorosilane.

The invention is illustrated in detail below, with reference to examples. If not stated otherwise, all parts are parts by weight:

EXAMPLE 1

Description of the apparatus:

The reaction for the preparation of dimethyldichlorosilane is carried out in a cascade consisting of two autoclaves which have identical dimensions and a capacity of 5 lit each and which are connected together by means of a pipeline which is as short as possible. The reaction mixture, which is to be described further below, is fed in continuously with the aid of a piston diaphragm pump. The pumping rate is controlled so that the total sojourn time of the reaction mixture in the cascade is three hours. The temperature of the two autoclaves is 350° C., and the pipeline between the two autoclaves is also heated to this temperature. The reaction pressure is regulated to a particular constant value (56 bar in this case) with the aid of a pneumatic regulating valve (which can be supplied by, for example, Kämmer GmbH, Essen). There is a relationship between the pressures set and the fullness of the apparatus. For example, when the pressure is regulated to a value of 56 bar, the apparatus is about 25% full (measured for the cold reaction mixture). If the apparatus is to be filled to a greater extent and hence higher throughputs achieved, higher pressures have to be accepted. The pipeline from the second autoclave to the valve is not heated, but is kept as short as possible so that the reaction mixture is still as hot as about 180° C. when the pressure is reduced. The reduction of the pressure from 56 bar to atmospheric pressure is carried out in one step. The product mixture is collected and is fed into a distillation apparatus to be worked up.

Description of the reaction mixture:

The reaction mixture employed contains the following components:
 68.6% of methyltrichlorosilane
 14.7% of a high-boiling non-cleavable residue
 14.7% of a low-boiling fraction having a high methyl content
 2% of aluminum chloride The high-boiling non-cleavable residue consists of, inter alia, the following disilanes which are capable of donating methyl groups: 18% of hexamethyl disilane, 18.4% of chloropentamethyldisilane, 11.7% of 1,2-dichlorotetramethyldisilane and 3.5% of 1,1,2-trichlorotrimethyldisilane. The low-boiling fraction having a high methyl content contains the following substances which are capable of donating methyl groups: 61.3% of tetramethylsilane and 11.9% of dimethylmonochlorosilane. To prepare the reaction mixture, the catalyst is dissolved in the high-boiling non-cleavable residue by stirring it in at 70° C. The solution thus obtained is cooled, after which the remaining components of the reaction mixture are added. As stated above, the pressure is adjusted to 56 bar, and the pumping rate is 0.8 liters/h. The crude product mixture collected contains 80% of components having a boiling point of below 80° C. Gas chromatography shows that the composition of this fraction is as follows: 58.3% of dimethyldichlorosilane, 5.2% of trimethylmonochlorosilane, 32.8% of methyltrichlorosilane, 2.0% of methyldichlorosilane and 1.7% of other low-boiling components (SiHCl$_3$, hydrocarbons). The relatively high-boiling residue (20% of the crude product) which has a high chlorine content and remains behind after the monomeric silanes have been distilled off is hydrolyzed by known methods and thus converted to a yellowish inert solid.

EXAMPLE 2

A mixture of 55 g of methyltrichlorosilane, 45 g of a high-boiling residue having a high methyl content, 5 g of a low-boiling fraction having a high methyl content and 4 g of sodium aluminum chloride is heated to 300° C. in an autoclave having a total volume of 0.5 liter, and is kept at this temperature for 4 hours, while stirring. The composition of the high-boiling and low-boiling fractions having a high methyl content correspond to those of Example 1. 57.6 g of a fraction which has a boiling point of below 80° C. and which contains the following monomeric silanes are obtained: 66.4% of dimethyldichlorosilane, 6.4% of trimethylmonochlorosilane and 24.3% of methyltrichlorosilane.

EXAMPLE 3

A mixture of 50 g of methyltrichlorosilane, 40 g of high-boiling non-cleavable residue, 20 g of a low-boiling fraction having a high methyl content and 2 g of aluminum chloride is heated to 300° C. in a 0.5 liter autoclave and is left at this temperature for 2 hours. The high-boiling residue contains the following substances having a high methyl content: 10.5% of hexamethyldisilane, 14.5% of chloropentamethyldisilane, 15.0% of 1,2-dichlorotetramethyldisilane and 6.2% of 1,1,2-trichlorotrimethyldisilane. The low-boiling fraction contains, as components having a high methyl content, 51.8% of tetramethylsilane and 20.9% of dimethylchlorosilane, 20.8% of trimethylchlorosilane, 54.4% of dimethyldichlorosilane and 3.6% of methyldichlorosilane, as well as 2.5% of other low-boiling components.

EXAMPLE 4

In the continuously operated apparatus described in Example 1, a mixture having the following composition is brought to reaction: 64.1% of methyltrichlorosilane, 8.7% of a high-boiling non-cleavable residue, 8.7% of a low-boiling fraction having a high methyl content, 9.0% of trimethylchlorosilane, 8.7% of methyldichlorosilane and 0.9% of aluminum chloride. The reaction temperature is 375° C., the pressure is 78 bar, and the pumping rate is adjusted so that a sojourn time of 2 h results. The high-boiling residue having a high methyl content contains the following components which are capable of donating methyl groups: 14.9% of hexamethyldisilane, 12.6% of chloropentamethyldisilane, 18.3% of 1,2-dichlorotetramethyldisilane and 16.5% of 1,1,2-trimethyltrichlorosilane. The low-boiling fraction contains, as components having a high methyl content, 67.3% of tetramethylsilane and 10.8% of dimethylchlorosilane. The crude product consists of 87.3% of a fraction which has a boiling point of below 80° C. and the following composition: 3% of trimethylchlorosilane, 59.1% of dimethyldichlorosilane, 31.7% of methyltrichlorosilane, 5% of methyldichlorosilane and 1.2% of other low-boiling compounds.

It will be understood that the specification and examples are illustrative but not limitative of the present invention and that other embodiments within the spirit and scope of the invention will suggest themselves to those skilled in the art.

We claim:

1. A process for the preparation of dimethyldichlorosilane from the low-boiling and high-boiling by-products of the direct synthesis of methylchlorosilanes, comprising reacting methyltrichlorosilane simultaneously with the low-boiling components having a high content of methyl groups and with the high-boiling non-cleavable components, in the presence of a catalyst, at a temperature between about 250° C. and 400° C. and under a pressure of up to 100 bar.

2. A process according to claim 1, wherein methyldichlorosilane or trimethylchlorosilane or both are also fed to the reaction.

3. A process according to claim 1, wherein the catalyst is aluminum chloride.

4. A process according to claim 1, wherein the process is carried out continuously.

* * * * *